(12) United States Patent
Tomasev et al.

(10) Patent No.: US 11,302,446 B2
(45) Date of Patent: Apr. 12, 2022

(54) PREDICTION OF FUTURE ADVERSE HEALTH EVENTS USING NEURAL NETWORKS BY PRE-PROCESSING INPUT SEQUENCES TO INCLUDE PRESENCE FEATURES

(71) Applicant: Google LLC, Mountain View, CA (US)

(72) Inventors: Nenad Tomasev, London (GB); Xavier Glorot, Montreal (CA); Jack William Rae, London (GB); Michal Zielinski, London (GB); Anne Mottram, London (GB); Harry Askham, London (GB); Andre Saraiva Nobre Dos Santos, London (GB); Clemens Ludwig Meyer, London (GB); Suman Ravuri, London (GB); Ivan Protsyuk, London (GB); Trevor Back, Saffron Walden (GB); Joseph R. Ledsam, London (GB); Shakir Mohamed, London (GB)

(73) Assignee: Google LLC, Mountain View, CA (US)

( * ) Notice: Subject to any disclaimer, the term of this patent is extended or adjusted under 35 U.S.C. 154(b) by 0 days.

(21) Appl. No.: 16/683,139

(22) Filed: Nov. 13, 2019

(65) Prior Publication Data
US 2020/0152333 A1     May 14, 2020

Related U.S. Application Data

(60) Provisional application No. 62/881,358, filed on Jul. 31, 2019, provisional application No. 62/760,768, filed on Nov. 13, 2018.

(51) Int. Cl.
*G16H 50/30*     (2018.01)
*G16H 70/60*     (2018.01)
(Continued)

(52) U.S. Cl.
CPC ............... *G16H 50/30* (2018.01); *G06N 3/08* (2013.01); *G16H 10/60* (2018.01); *G16H 50/50* (2018.01); *G16H 70/60* (2018.01)

(58) Field of Classification Search
CPC ........ G16H 50/30; G16H 50/50; G16H 10/60; G16H 70/60; G06N 3/08; G06N 20/20; G06N 3/0445; G06N 3/0454
See application file for complete search history.

(56) References Cited

U.S. PATENT DOCUMENTS

2017/0032241 A1    2/2017   Corrado et al.
2017/0147777 A1*   5/2017   Kim ...................... G16H 50/30
(Continued)

FOREIGN PATENT DOCUMENTS

WO    WO 2014/201515     12/2014
WO    WO 2017/172629     10/2017

OTHER PUBLICATIONS

Edward Choi, Mohammad Taha Bahadori, Andy Schuetz, Walter F. Stewart, Jimeng Sun, "Doctor AI: Predicting Clinical Events via Recurrent Neural Networks" Proceedings of Machine Learning for Healthcare, JMLR vol. 56, p. 301-318 (pdf pages not numbered), © 2016 (Year: 2016).*

(Continued)

*Primary Examiner* — Gregory D. Moseley
(74) *Attorney, Agent, or Firm* — Fish & Richardson P.C.

(57) ABSTRACT

Methods, systems, and apparatus, including computer programs encoded on computer storage media, for predicting future adverse health events using neural networks. One of the methods includes receiving electronic health record data for a patient; generating, from the electronic health record data, an input sequence comprising a respective feature representation at each of a plurality of time window time steps, comprising, for each time window time step: determining, for each of the possible numerical features, whether (Continued)

the numerical feature occurred during the time window; and generating, for each of the possible numerical features, one or more presence features that identify whether the numerical feature occurred during the time window; and processing the input sequence using a neural network to generate a neural network output that characterizes a predicted likelihood that an adverse health event will occur to the patient.

25 Claims, 3 Drawing Sheets

(51) Int. Cl.
  *G16H 50/50* (2018.01)
  *G16H 10/60* (2018.01)
  *G06N 3/08* (2006.01)

(56) References Cited

U.S. PATENT DOCUMENTS

| | | | |
|---|---|---|---|
| 2017/0308981 A1* | 10/2017 | Razavian | G06Q 10/10 |
| 2018/0075343 A1 | 3/2018 | van den Oord et al. | |
| 2018/0277246 A1* | 9/2018 | Zhong | G06F 16/3329 |
| 2019/0180882 A1* | 6/2019 | Han | G16H 50/20 |
| 2019/0228291 A1* | 7/2019 | Kurasawa | G06F 17/16 |
| 2019/0362494 A1* | 11/2019 | Wang | A61B 6/504 |

OTHER PUBLICATIONS

Bakshi Rohit Prasad and Sonali Agarwal, "Modeling Risk Prediction of Diabetes", 2014 9th International Conference on Industrial and Information Systems (ICIIS), date of conference: Dec. 15-17, 2014, date added to IEEE Xplore: Feb. 12, 2015, available at https://ieeexplore.ieee.org/document/7036646 (Year: 2014).*
Miguel A. Bautista, Artsiom Sanakoyeu, et al., "Deep Unsupervised Similarity Learning using Partially Ordered Sets" dated by archive. org as having been available on Aug. 8, 2017. (Year: 2017).*
Alistair E. W. Johnson, et al., "Machine Learning and Decision Support in Critical Care", Proc IEEE Inst Electr Electron Eng. Feb. 2016 ; 104(2): 444-466. doi:10.1109/JPROC. 2015.2501978 (Year: 2016).*
Abadi et al., "TensorFlow: Large-Scale Machine Learning on Heterogeneous Distributed Systems," https://arxiv.org/abs/1603.04467, Mar. 2016, 19 pages.
Alaa et al., "Personalized Risk Scoring for Critical Care Prognosis Using Mixtures of Gaussian Processes," IEEE Transactions on Biomedical Engineering, Jan. 2018, 65(1): 12 pages.
Alge et al., "Biomarkers of AKI: A Review of Mechanistic Relevance and Potential Therapeutic Implications," Clinical Journal of American Society Nephrology, Januaiy 2015, 10(1): 147-155.
Avati et al., "Improving palliative care with deep learning," 2017 IEEE International Conference on Bioinformatics and Biomedicine (BIBM), Nov. 2017, 311-316.
Bihorac et al., "MySurgeryRisk: Development and Validation of a Machine-learning Risk Algorithm for Major Complications and Death After Surgery," Annals of Surgery, Apr. 2019, 269(4): 11 pages.
Bradbury et al., "Quasi-Recurrent Neural Networks," International Conference on Learning Representations, Mar. 2017, 12 pages.
Brier, "Verification of forecasts expressed in terms of probability," Monthly Weather Review, dated Apr. 1950, 78(1): 1-3.
Caruana et al., "Using the Future to "Sort Out" the Present: Rankprop and Multitask Learning for Medical Risk Evaluation," Advances in Neural Information Processing Systems, 1996, 9: 959-965.
Chen et al., "Why Is My Classifier Discriminatory?," https://arxiv.org/abs/1805.12002, May 2018, 17 pages.
Cheng et al., "Risk Prediction with Electronic Health Records: A Deep Learning Approach,"Proceedings of the 2016 SIAM International Conference on Data Mining, Jun. 2016, 9 pages.
Cheng et al., "Predicting Inpatient Acute Kidney Injury over Different Time Horizons: How Early and Accurate?," AMIA Annual Symposium Proceedings, 2017, 565-574.
Chung et al., "Empirical Evaluation of Gated Recurrent Neural Networks on Sequence Modeling," https://arxiv.org/abs/1412.3555, Dec. 2014, 9 pages.
Collins et al., "Capacity and Trainability in Recurrent Neural Networks," International Conference on Learning Representations, Mar. 2017, 17 pages.
De Fauw et al., "Clinically applicable deep learning for diagnosis and referral in retinal disease," Nature Medicine, Aug. 2018, 24: 1342-1350.
Department of Veterans Affairs, "Veterans Health Administration: Providing Health Care for Veterans," retrieved on Dec. 31, 2019, retrieved from URL <Https://www.va.gov/health/>, 4 pages.
Ding et al., "The Effectiveness of Multitask Learning for Phenotyping with Electronic Health Records Data," https://arxiv.org/abs/1808.03331v2, revised Oct. 2018, 13 pages.
Futoma et al., "Learning to detect sepsis with a multitask gaussian process RNN classifier," Proceedings of the International Conference on Machine Learning, Aug. 2017, 70: 9 pages.
Glorot et al., "Understanding the difficulty of training deep feed forward neural networks," International Conference on Artificial Intelligence and Statistics, Mar. 2010, 9: 249-256.
Graves et al., "Hybrid computing using a neural network with dynamic external memory," Nature, Oct. 2016, 538: 471-476.
Graves et al., "Neural Turing Machines," https://arxiv.org/abs/1410.5401, last revised Dec. 2014, 26 pages.
Guo et al., "On Calibration of Modern Neural Networks," Proceedings of the 34th International Conference on Machine Learning, Aug. 2017, 14 pages.
Henry et al., "A targeted real-time early warning score (TREWScore) for septic shock," Science Translational Medicine, Aug. 2015, 7(299): 299ra122: 9 pages.
Hochreiter et al., "Long Short-Term Memory," Neural Computation, Nov. 1997, 9(8): 1735-1780.
Johnson et al., "Machine Learning and Decision Support in Critical Care," Proceedings of the IEEE, Feb. 2016, 104(2): 444-466.
Khwaja, "KDIGO Clinical Practice Guidelines for Acute Kidney Injury," Nephron Clinical Practice, Aug. 2012, 120(4), c179-c184.
Kidney Disease: Improving Global Outcomes (KDIGO) Acute Kidney Injury Work Group, "KDIGO Clinical Practice Guideline for Acute Kidney Injury," Kidney International Supplements, Mar. 2012, 2(1): 141 pages.
Kingma et al., "Adam: A Method for Stochastic Optimization," https://arxiv.org/abs/1412.6980v8, Jul. 2015, 15 pages.
Komorowski et al., "The Artificial Intelligence Clinician learns optimal treatment strategies for sepsis in intensive care," Nature Medicine, Oct. 2018, 24: 11 pages.
Koyner et al., "Development of a Multicenter Ward-Based AKI Prediction Model," Clinical Journal of the American Society of Nephrology, Nov. 2016, 11: 1935-1943.
Koyner et al., "The Development of a Machine Learning Inpatient Acute Kidney Injury Prediction Model," Critical Care Medicine, Jul. 2018, 46(7): 8 pages.
Lachance et al., "Association between e-alert implementation for detection of acute kidney injury and outcomes: a systematic review," Nephrology Dialysis Transplantation, Jan. 2017, 32(2): 265-272.
Lakshminarayanan et al., "Simple and Scalable Predictive Uncertainty Estimation using Deep Ensembles," https://arxiv.org/abs/1612.01474, last revised Nov. 2017, 15 pages.
Lei et al., "Training RNNs as Fast as CNNs," arXiv Preprint arXiv: 1709.02755, Sep. 2017, 14 pages.
Lim et al., "Disease-Atlas: Navigating Disease Trajectories using Deep Learning," Proceedings of Machine Learning Research, Aug. 2018, 85: 23 pages.
Lipton et al., "Learning to Diagnose with LSTM Recurrent Neural Networks," https://arxiv.org/abs/1511.03677v6, Mar. 2016, 18 pages.
MacLeod, "NCEPOD report on acute kidney injury—must do better," The Lancet, Oct. 2009, 374(9699): 1405-1406.
Mann et al., "On a Test of Whether one of Two Random Variables is Stochastically Larger than the Other," The Annals of Mathematical Statistics, Mar. 1947, 18(1): 50-60.

(56) References Cited

OTHER PUBLICATIONS

Miotto et al., "Deep Patient: An Unsupervised Representation to Predict the Future of Patients from the Electronic Health Records," Scientific Reports, May 2016, 10 pages.

Mohamadlou et al., "Prediction of Acute Kidney Injury With a Machine Learning Algorithm Using Electronic Health Record Data," Canadian Journal of Kidney Health And Disease, Jun. 2018, 9 pages.

Niculescu-Mizil et al., "Predicting good probabilities with supervised learning," Proceedings of the International Conference on Machine Learning, Aug. 2005, 625-632.

Pan et al., "A Self-Correcting Deep Learning Approach to Predict Acute Conditions in Critical Care," https://arxiv.org/abs/1901.04364, Jan. 2019, 8 pages.

Park et al., "Impact of Electronic Acute Kidney Injury (AKI) Alerts With Automated Nephrologist Consultation on Detection and Severity of AKI: A Quality Improvement Study," American Journal of Kidney Diseases, Jan. 2018, 71(1): 9-19.

Perotte et al., "Risk prediction for chronic kidney disease progression using heterogeneous electronic health record data and time series analysis," Journal of the American Medical Informatics Association, Jul. 2015, 22:872-880.

Platt, "Probabilistic outputs for support vector machines and comparisons to regularized likelihood methods," Advances in Large-Margin Classifiers, Mar. 1999, 11 pages.

Rajkomar et al., "Scalable and accurate deep learning with electronic health records," NPJ Digital Medicine, May 2018, 10 pages.

Razavian et al., "Temporal Convolutional Neural Networks for Diagnosis from Lab Tests," https://arxiv.org/abs/1511.07938, Mar. 2016, 19 pages.

Saito et al., "The Precision-Recall Plot Is More Informative than the ROC Plot When Evaluating Binary Classifiers on Imbalanced Datasets," PLoS ONE, Mar. 2015, 21 pages.

Santoro et al., "Relational recurrent neural networks," Advances in Neural Information Processing Systems 31, Dec. 2018, 12 pages.

Santoro et al., "Meta-learning with memory-augmented neural networks," Proceedings of the International Conference on Machine Learning, Jun. 2016, 9 pages.

Schulam et al., "Reliable decision support using counterfactual models," Advances in Neural Information Processing Systems, Dec. 2017, 12 pages.

Soleimani et al., "Treatment-response models for counterfactual reasoning with continuous-time, continuous-valued interventions," https://arxiv.org/pdf/1704.02038.pdf, Nov. 2017, 11 pages.

Srivastava et al., "Highway Networks," https://arxiv.org/abs/1505.00387, last revised Nov. 2015, 6 pages.

Stenhouse et al., "Prospective evaluation of a modified early warning score to aid earlier detection of patients developing critical illness on a general surgical ward," The British Journal of Anaesthesia, May 2000, 84(5): 34 pages.

Telenti et al., "Rethinking the medical record," The Lancet, Mar. 2018, 391: 1013.

Thomson et al., "Safer care for the acutely ill patient: Learning from serious incidents," National Patient Safety Agency, Oct. 2007, retrieved from URL <https://studylib.net/doc/18230206/safer-care-for-the-acutely-ill-patient>, 48 pages.

Wang et al., "Acute Kidney Injury and Mortality in Hospitalized Patients," American Journal of Nephrology, May 2012, 35: 349-355.

Wiens et al., "Patient Risk Stratification with Time-Varying Parameters: A Multitask Learning Approach," Journal of Machine Learning Research, Apr. 2016, 23 pages.

Zadrozny et al., "Transforming classifier scores into accurate multiclass probability estimates," Proceedings of the eighth ACM SIGKDD International Conference on Knowledge Discovery and Data Mining, Jul. 2002, 694-699.

Zilly et al., "Recurrent highway networks," Proceedings of the International Conference on Machine Learning, Aug. 2017, 70: 10 pages.

PCT International Search Report and Written Opinion in International Appln. No. PCT/US2019/061294, dated Mar. 5, 2020, 21 pages.

Razavian et al., "Multi-task Prediction of Disease Onsets from Longitudinal Lab Tests," Proceedings of Machine Learning for Healthcare, Dec. 2016, 56:27 pages.

PCT International Preliminary Report on Patentability in International Application No. PCT/US2019/061294, dated May 27, 2021, 15 pages.

\* cited by examiner

PREDICTION OF FUTURE ADVERSE HEALTH EVENTS USING NEURAL NETWORKS BY PRE-PROCESSING INPUT SEQUENCES TO INCLUDE PRESENCE FEATURES

CROSS-REFERENCE TO RELATED APPLICATIONS

This application claims priority to U.S. Provisional Application No. 62/760,768, filed on Nov. 13, 2018, and claims priority to U.S. Provisional Application No. 62/881,358, filed on Jul. 31, 2019. The disclosures of the prior applications are considered part of and are incorporated by reference in the disclosure of this application.

BACKGROUND

This specification relates to processing inputs using a neural network.

Neural networks are machine learning models that employ one or more layers of nonlinear units to predict an output for a received input. Some neural networks include one or more hidden layers in addition to an output layer. The output of each hidden layer is used as input to the next layer in the network, i.e., the next hidden layer or the output layer. Each layer of the network generates an output from a received input in accordance with current values of a respective set of parameters.

SUMMARY

This specification describes a system that makes predictions that characterize the likelihood that a specific adverse health event will occur to a patient in the future. The predictions are made based on electronic health record data for the patient. In particular, the system generates, from the electronic health record data, an input sequence that includes a respective feature representation at each of a plurality of time window time steps and processes the input sequence using a neural network to generate a neural network output. The neural network output includes data that characterizes a predicted likelihood that an adverse health event will occur to the patient after the last time window time step in the input sequence. Using the described techniques, clinicians can be provided with accurate prediction data that can then allow the clinicians to effectively treat the patient, e.g., by taking preventative action in advance of the adverse health event actually occurring.

Thus in one aspect there is provided a system comprising one or more computers and one or more storage devices storing instructions that, when executed by the one or more computers, cause the one or more computers to perform operations comprising receiving electronic health record data for a patient, the electronic health data comprising a plurality of features representing health events in an electronic health record for the patient, each of the plurality of features belonging to a vocabulary of possible features that comprises a plurality of possible numerical features and a plurality of possible discrete features. The operations may further comprise generating, from the electronic health record data, an input sequence comprising a respective feature representation at each of a plurality of time steps, wherein the plurality of time steps comprises a respective time window time step for each of a plurality (succession) of time windows. The generating may comprise, for each time window time step, determining, for each of the possible numerical features and from the electronic health record data, whether the numerical feature occurred during the time window corresponding to the window time step. The generating may further comprise, for each time window time step, generating, for each of the possible numerical features, one or more presence features that identify whether the numerical feature occurred during the time window corresponding to the time window time step. The generating may further comprise, for each time window time step, including the one or more possible presence features in the feature representation for the time step. The operations may further comprise processing the input sequence using a neural network to generate a neural network output that characterizes a predicted likelihood that an adverse health event will occur to the patient after the time window corresponding to the last time window time step in the input sequence.

Implementations of the system address a problem of processing electronic health record data using a neural network, e.g., to train the neural network or to infer the risk of an adverse health event using a (trained) neural network. Electronic health record data typically has not been generated with processing by a neural network in mind, and much of the data may be unsuitable for such processing. However simply disregarding unsuitable data is undesirable. Implementations of the system facilitate processing electronic health record data more efficiently using a neural network, and hence facilitate better predictions by the neural network e.g., a greater percentage of correct predictions for a defined proportion of false alerts.

More specifically some implementations of the system address the problem of the typical sparsity of electronic health record (EHR) data as compared with the granularity of the time windows representing co-occurring events. One approach would be to impute the missing data, but this can be unreliable e.g., where different labs are used for the same measurement, and more generally does not appear to provide a consistent benefit. In implementations, therefore, presence features are generated which enable the neural network to distinguish between the absence of a numerical feature (value) and an actual value of zero. Put differently, a presence feature may be considered to capture a feature associated with an act of making a measurement, whatever the outcome. Thus, for example, a presence feature may be a binary feature. The presence features may also encode discrete features such as the implementation of diagnostic or other medical procedure codes. This approach facilitates better use of EHR data by a neural network for predicting the likelihood of an adverse health event.

In some EHR data explicit numerical values may not be recorded, especially if a value is considered normal. To address this values of a numerical feature may be partitioned into a plurality of ranges, and a presence feature may then encode a range to which the numerical feature belongs (in particular where the electronic health record data identifies only the range to which the numerical feature belongs). For example a presence feature may encode whether a numerical value is considered to be normal, high, or low (or very high or very low). This facilitates processing EHR data even where numerical values are absent from the record. Numerical features may be normalized to the range [0,1] and capped at e.g., the 1% and 99% percentiles to avoid data entry errors dominating. In some implementations the feature representation for a time step includes both a numerical value of a numerical feature and the one or more presence features for the numerical feature.

Another typical characteristic of EHR data is that it can be sparse, sometimes very sparse. In some implementations the system may determine that the electronic health data does not identify any features as occurring during a time window corresponding to a particular time window time step, and may then generate a feature representation that indicates that no features occurred during the corresponding time window. This can help the neural network to respond to patterns of missing features and can also help the neural network to operate in a consistent manner when predicting that an adverse health event will occur within a time period after the last time window time step. In some implementations such a feature representation may only be generated for current rather than historical EHR data, e.g., when the system is continuously updating the predicted likelihood of an adverse health event such as during an inpatient stay. In implementations the neural network provides a predicted likelihood of an adverse health event for each of a succession of time window time steps, including time window time steps for which numerical features are absent: Even where there is no new measurement the prediction may be updated; this updating may, for example, rely on features from a surrogate time step as described below.

A further characteristic of EHR data which presents a challenge for neural network processing is that for a large proportion of the features there may be no very exact time stamp. For example the date of a feature may be known, but not its time of day. Thus in implementations the plurality of time steps may include one or more surrogate time steps, each associated with a plurality of time window time steps that immediately precede the surrogate time step in the input sequence. For example there may be a surrogate time step at the conclusion of each day. Then generating the feature representation may comprise, for each of the surrogate time steps, determining whether the EHR data identifies any features (i) as occurring during a time interval spanned by the time windows corresponding to the plurality of time window time steps associated with the surrogate time steps without (ii) identifying a specific time window during which the feature occurred, and if so generating the feature representation for the surrogate time step from such features. In implementations the neural network processes such features at a current time step but the neural network output is not used for predicting an adverse health event until at least the next time step.

As mentioned, the EHR data can be sparse and it is therefore desirable to use the information in this data efficiently. One way to do this is to capture higher-level semantics from the data. Therefore in some implementations the features include clinical features which are each mapped to a corresponding high-level concept. Here a high-level concept may correspond to one or a set of predefined categories to which a clinical feature can be assigned, where each category may contain multiple different clinical features. A histogram of frequencies of each high-level concept may then be used by the system in the feature representation for the time window time step.

The feature representation at each of the time window time steps may also include at least one aggregate historical feature representation, e.g., two such representations aggregated over different time periods such as a recent time period, e.g., 48 hours, and a period comprising an entirety of the EHR data. Other features may include an age feature based on an age of the patient as of the time window corresponding to the time window time step, and a time feature identifying the time window corresponding to the time window time step e.g. in 6 hour buckets. Further features may include one or more baseline values for numerical (measurement) features, which may be dependent on other features e.g., age.

In implementations the neural network comprises a deep embedding neural network to embed the features in the feature representation in an embedding space. The neural network output may then be generated from the embedded features. For example the deep embedding neural network may comprise a plurality of fully-connected layers (though other architectures may be used). A first deep embedding neural network may embed (EHR) features from a current time step and a second first deep embedding neural network may embed historical features from historical EHR data. In some implementations the deep embedding neural network has residual connections between the fully-connected layers; it may be L1 regularized during training.

In implementations the neural network is configured to implicitly model the historical context of the EHR data for the patient by modifying an internal representation (or state) through time. For example in some implementations the neural network may comprise a recurrent neural network e.g., with a plurality of recurrent neural network (RNN) layers and, optionally, highway connections. In other implementations the neural network may comprise a temporal convolutional neural network. The recurrent neural network may have an input comprising the embedded features generated by the deep embedding neural network(s).

In implementations the neural network output includes at least a first score that characterizes a predicted likelihood that the adverse health event will occur to the patient within a first time period after the time window corresponding to the last time window time step, and may include a second score that characterizes a predicted likelihood that the adverse health event will occur to the patient within a second, longer time period after the time window corresponding to the last time window time step. The neural network may then include a cumulative distribution function layer configured to generate a cumulative score distribution over at least the first time window and the second time window that requires the second score to be higher than the first score, to encourage monotonicity of the predicted likelihood.

In implementations the neural network output includes one or more auxiliary outputs for one or more auxiliary value-prediction tasks. For example an auxiliary task may be to predicted a maximum future observed value for a medical test that is correlated with the adverse health event or to provide some other statistics of future observed values, e.g., mean, median, or mode. In some implementations auxiliary outputs may be used only during training of the neural network, but in other implementations the auxiliary outputs of one or more auxiliary tasks may be presented to a user, e.g., to provide insight and explainability for a predicted adverse health event.

The operations performed by the system may include determining whether the neural network output indicates that the predicted likelihood exceeds a threshold and, when the neural network output indicates that the predicted likelihood exceeds a threshold, transmitting an alert for presentation to a user. For example the alert may indicate that a doctor should examine the patient because they are at risk of the adverse health event. Also or instead the operations performed by the system may include generating user interface data from the neural network output, and outputting this for presentation to a user. For example the user interface data may be suitable for identifying one or more patients at greatest risk of the adverse health event, for triage. The alert, or user interface data, may indicate risk of the adverse health event occurring within the previously mentioned first and/or second time periods.

The system may thus be used for evaluating the condition of a patient to identify or detect a condition in which the patient has an incipient (but not yet readily apparent) adverse health event. The system may also be used for providing a particular treatment to a patient after such a condition has been identified, i.e., by treating the patient for the adverse health event.

The operations performed by the system may include obtaining new electronic health record data comprising features occurring at a next time window immediately after the last time window corresponding to the last time window time step in the input sequence, generating a new feature representation from the new electronic health record data, and processing the new feature representation using the neural network generate a new neural network output. In this way the system may be used for continuous monitoring of a patient e.g., an inpatient.

In one merely exemplary implementation the adverse health event comprises Acute Kidney Injury (AKI), of any severity stage e.g., KDIGO (Kidney Disease: Improving Global Outcomes guidelines) stage 1, 2 or 3. However the described data pre-processing, e.g., to obtain embedded features, may be applied to EHR data of any type—that is, the techniques described herein are usable for pre-processing data which is often unsuitable for processing by a neural network for the reasons given previously to generate embedded features which are readily processed by a neural network. This pre-processing can be useful irrespective of the higher layers of neural network processing which are applied and the specific clinical or other purpose for which they system might be trained overall.

Particular embodiments of the subject matter described in this specification can therefore be implemented so as to realize one or more of the following advantages.

Electronic health record data, i.e., data derived from the electronic health record of a patient, is highly-sparse due to asynchronous measurements that are not present at each time step. For example, while a vocabulary of possible features that represent events that could occur during any given time window may include over one hundred thousand features, at each time window less than one percent of those features actually occur on average and, during some time windows, no features may occur. Additionally, electronic health record data may not include specific time stamps for all of the events represented by the features in the vocabulary. For example, for some events, the electronic health record may identify the day that the event occurred without identifying the particular time window during the day during which the event occurred.

Because of this, electronic health record data is not readily adapted to be processed by a neural network in order to make accurate predictions.

The described systems pre-process the features in the electronic health record data in order to generate input sequences that can be effectively processed by a neural network. By employing the pre-processing techniques described in this specification, a neural network can effectively and accurately predict the risk that an adverse health event will occur well in advance of the health event actually occurring. Accordingly, by employing the described pre-processing techniques, clinicians can be provided with accurate prediction data that can then allow them to effectively treat the patient, e.g., by taking preventative action in advance of the adverse health event actually occurring.

In particular, the described systems pre-process the data to account for the sparsity by augmenting the feature representation at each time window time step with one or more presence features for each possible numerical feature. Numerical features are features that have numerical values that may be any value within some range, e.g., as opposed to discrete features (e.g., binary features that identify whether an event occurred or didn't occur or categorical features that identify that an event belongs to one of a fixed, discrete set of categories). Examples of numerical features include laboratory test results and readings or measurements from medical devices, e.g., body temperature readings.

Additionally, the described systems generate feature representations even at time steps for which no features occurred during the corresponding time window. That is, a feature representation identifying that no features occurred during the time window is provided as input to the neural network at a time window time step corresponding to the time window, allowing the neural network to nonetheless make an accurate prediction regarding potential feature adverse health events after the expiration of the "empty" time window.

Moreover, the input sequence is augmented with surrogate time steps that collect features representing events for which specific time stamps are not available in the electronic health record data. Because no specific time stamps are associated with the events represented by features collected at the surrogate time step, the output of the neural network for that time step may be discarded, but the neural network nonetheless updates its internal state in order to improve the accuracy of predictions made at future time window time steps.

The details of one or more embodiments of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
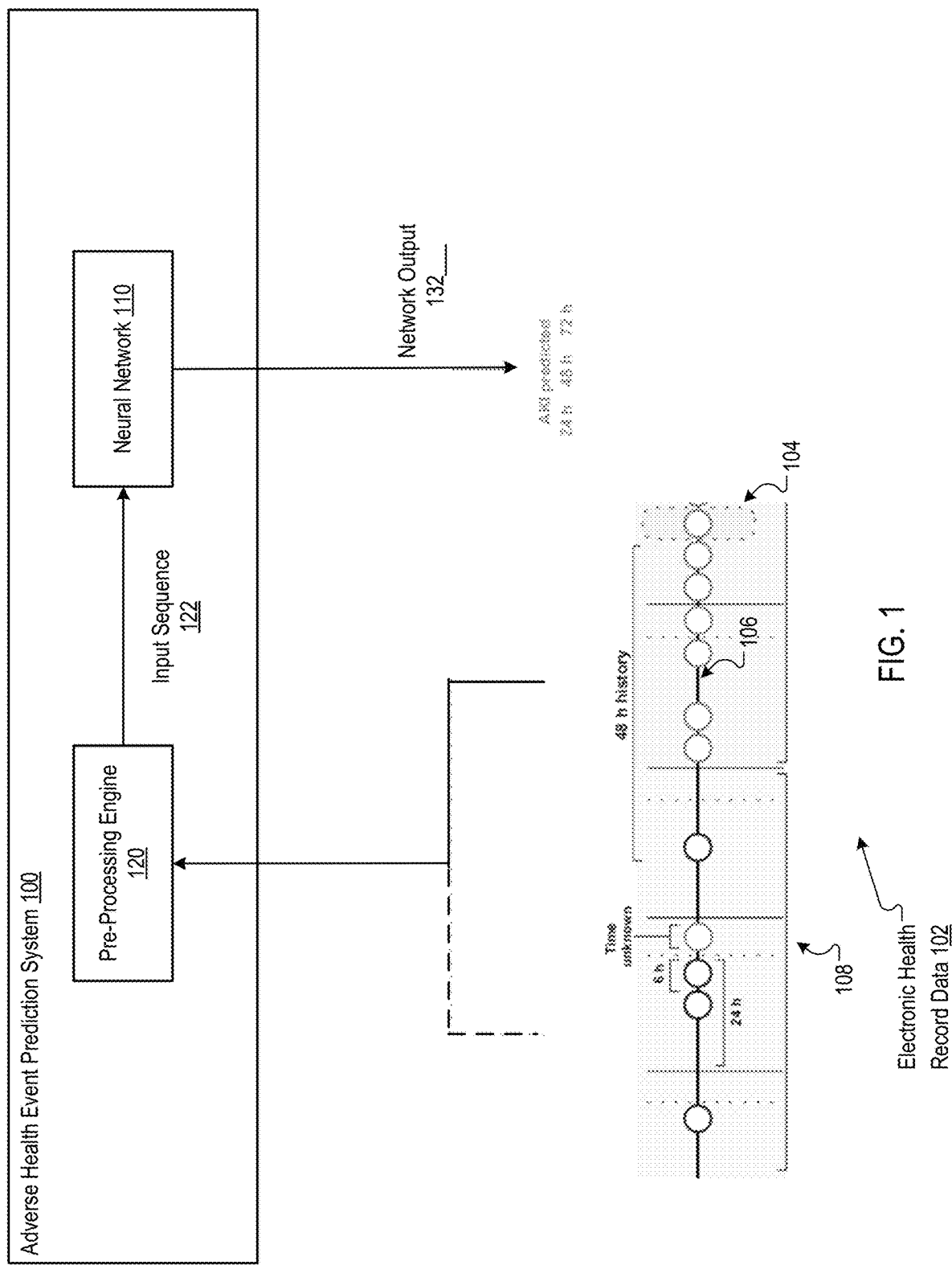
FIG. 1 shows an example adverse health event prediction system.

FIG. 1 shows an example adverse health event prediction system 100. The adverse health event prediction system 100 is an example of a system implemented as computer programs on one or more computers in one or more locations in which the systems, components, and techniques described below are implemented.

The system 100 makes predictions that characterize the likelihood that a specific adverse health event will occur to a patient in the future. The predictions are made based on electronic health record data 102 for the patient.

Generally, an adverse health event is an event that can occur to a patient that is likely to adversely impact the health of the patient. In the example of FIG. 1, the adverse health event is an acute kidney injury (AKI). Other examples of adverse health events whose likelihoods can be predicted by the system 100 include sepsis, a patient health deterioration event, an abnormal physiological sign, readmission to a medical care facility, a discharge from a medical care facility (i.e., a likelihood that the patient will be unsafely discharged), an admission to an intensive care unit (ICU), mortality, and so on.

In particular, the system 100 receives electronic health record data 102 for a patient, generates an input sequence 122 from the electronic health record data 102, and then processes the input sequence 122 using a neural network 110 to generate a neural network output 132.

For example, the neural network output 132 can include a score, e.g., a probability, that characterizes a predicted likelihood that the adverse health event will occur to the patient within a fixed time period after the last time window in the electronic health record data 102. As another example, the neural network output 132 can include scores for multiple time periods, each starting after the last time window in the health record data 102 and each being a different length. The score for each time period can be a score, e.g., a probability, that characterizes the predicted likelihood that the adverse health event will occur to the patient within the corresponding time period after the last time window in the health record data 102.

As a particular example, in FIG. 1 the neural network output 132 includes one score for the 24 hours following the last time window in the data 102, another score for the 48 hours following the last time window in the data 102, and another score for the 72 hours following the last time window in the data 102. The score for the following 48 hours, for example, represents the likelihood that the patient will experience AKI within the 48 hour time window following the last time window in the data 102.

The electronic health record data 102 for the patient includes a plurality of features representing health events in an electronic health record for the patient, with each of the plurality of features belonging to a vocabulary of possible features. This vocabulary of possible features includes both possible numerical features and possible discrete features. In other words, the vocabulary includes some features that are numerical features and some features that are discrete features.

Numerical features are features that have numerical values that may be any value within some range, while discrete features include binary features, e.g., features that indicate whether events did or did not occur, and other features that can only take one of a small number of possible values, e.g., categorical features. Examples of numerical features include laboratory test results or patient vital sign measurements, i.e., measurements of vital signs captured by a medical device, both of which can take many possible different values. Examples of discrete features, on the other hand, include binary features like whether the patient was admitted for treatment during a given time period or categorical features like procedural codes assigned to a particular procedure or event.

In the example of FIG. 1 and for ease of description, the electronic health record data 102 is depicted as a sequential representation of health events, with events being ordered by the time that the events occurred and represented by circles. However, in practice, the health record data 102 can be received by the system 100 in any appropriate format that identifies the features that represent health events in the electronic health record for the patient and includes information about the time at which the health events occurred.

Generally, the sequence 122 generated from the health record data 102 by the system includes a feature representation at each of a number of time window time steps. A time window time step is a time step that corresponds to a time window, with each time window time step corresponding to a different time window. The feature representation at any given time window time step is generated from features occurring at the corresponding time window. For example, the sequence 122 can include time window time steps for all time windows starting from the earliest health event in the health record data 102 or time window time steps for all time windows that are within a threshold time period of the most recent health event in the health record data 102.

In the example of FIG. 1, the sequence 122 includes a respective representation for each of multiple 6 hour time windows, a circle indicating one or more health events in a time window. The sequential representation shown in FIG. 1 is therefore divided into 6 hour time windows.

As can be seen in the sequential representation shown in FIG. 1, the electronic health record data 102 is not well adapted for processing by the neural network 110.

In particular, the electronic health record data 102 in particular and electronic health record data in general is highly-sparse due to asynchronous measurements that are not present at each time step.

For example, while the vocabulary of possible features that represent events that could occur during any given time window may include over one hundred thousand features, with many of these being numerical features, less than one percent of those features actually occur on average in any given time window. For example, although at the current time window 104, i.e., the most recent time window in the health record data 102, one or more events occurred, these events generally impact only a very small number of the hundreds of thousands of features.

Additionally, during some time windows, no features may occur. For example, as shown in FIG. 1, no health events occurred during the six hour time window 106. However, the neural network 110 nonetheless needs to make accurate predictions even when no health events occurred during the most recent time window.

Moreover, electronic health record data may not include specific time stamps for all of the events represented by the features in the vocabulary. For example, for some events, the electronic health record may identify the day that the event occurred without identifying which particular time window during the day the event occurred during. As a particular example, for the events shown as occurring in time window 108, no time stamp is included in the health record data 102 that identifies the specific time at which the events occurred. Instead, the health record data 102 identifies only the day at which the health events occurred. Thus, the system 100 cannot accurately place the events as occurring during any one six hour time window.

Because of this, electronic health record data is not readily adapted to be processed by the neural network 110 in order to make accurate predictions, i.e., to generate accurate neural network outputs 132.

Instead, the system 100 pre-processes the features in the electronic health record data in order to generate input sequences 122 that can be effectively processed by the neural network 110. By employing the pre-processing techniques described in this specification, the neural network 110 can effectively and accurately predict the risk that an adverse health event will occur well in advance of the health event actually occurring. Accordingly, by employing the described pre-processing techniques, clinicians can be provided with accurate prediction data that can then allow them to effectively treat the patient, e.g., by taking preventative action in advance of the adverse health event actually occurring.

Generating an input sequence 122 from electronic health record data 102 in a manner that ensures that the neural network 110 can generate accurate predictions about the patient's future health is described in more detail below with reference to FIG. 3.

Once the neural network output 132 has been generated, the system 100 can determine whether any of the scores in the output 132 exceed a corresponding threshold and, if so, transmit an alert for presentation to a user, e.g., to a user computer of a physician or other medical personnel. When there are multiple scores in the neural network output 132, the scores corresponding to different time periods can have the same threshold value or different threshold values.

Alternatively or in addition, the system 100 can generate a user interface presentation based on the data in the neural network output 132, e.g., a presentation that conveys the patient's risk for having the adverse health event, and then provide the user interface presentation for display on the user computer.

In some implementations, the system 100 continually updates the neural network output 132 as new electronic health record data for the patient becomes available. For example, the system 100 can generate an initial input sequence and generate an initial neural network output when a patient is admitted for treatment or at another initial time point. The system 100 can then obtain new data at the expiration of each subsequent time window and generate updated neural network outputs for each of the subsequent time windows until the patient is discharged or until some other termination criteria are satisfied.

In some cases, the neural network 110 can be an ensemble of individual neural networks and the neural network output 132 can be a combination, e.g., an average, of the neural network outputs generated by the individual neural networks in the ensemble. For example, the neural networks in the ensemble may have been trained on different data, may have somewhat different architectures, or both. In some cases, the neural network output 132 can be a weighted average of the neural network outputs generated by the networks in the ensemble, and the weights can be determined by, after training, calibrating the weights using isotonic regression to reflect the frequency of observed outcomes.

In these cases, the neural network output 132 can also include a measure of uncertainty that is based on the deviation or variance between the individual neural network outputs generated by the individual neural networks. The measure of uncertainty, e.g., the standard deviation of the individual neural network outputs, the variance of the individual neural network outputs range of the individual neural network outputs, or the range of the individual neural network outputs, can be computed from all of the individual outputs or from some subset of the individual outputs that does not include outliers, e.g., all of the outputs except for a fixed number of highest and lowest values. The system can then provide this measure of uncertainty to the user along with the alert or as part of the user interface presentation.

Figure 2:
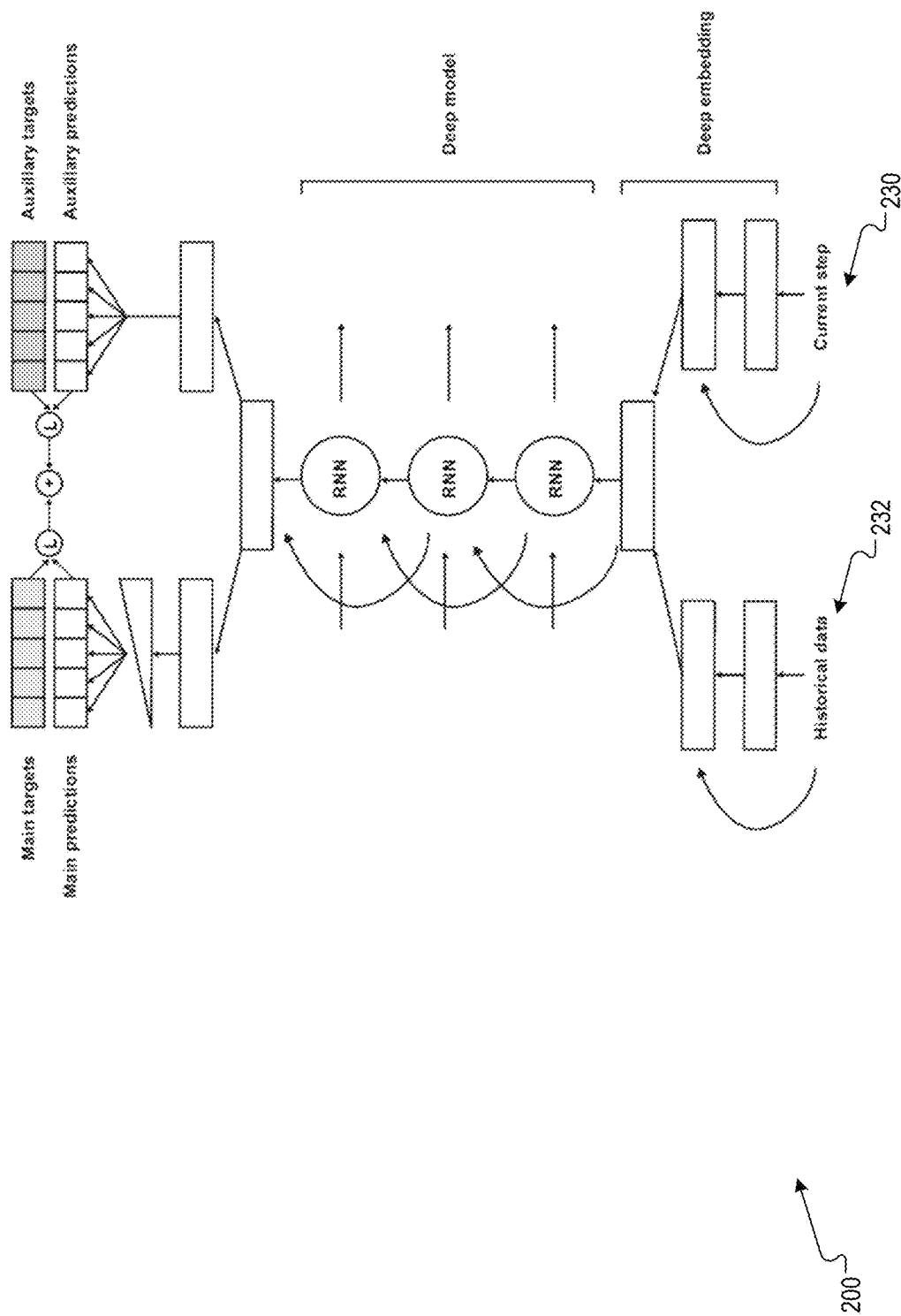
FIG. 2 shows an example architecture of the neural network used by the health event prediction system.

FIG. 2 shows an example architecture of the neural network 110 used by the adverse health event prediction system 100. When there are multiple individual neural networks in an ensemble, the architecture shown in FIG. 2 can be the architecture of one of the individual neural networks in the ensemble. In some of these cases, all of the neural networks in the ensemble can have the same architecture, i.e., the architecture shown in FIG. 2, but be trained on different training data.

In particular, the example of FIG. 2 shows the processing of the neural network 110 at a current time step, i.e., a time step corresponding to a current time window. At the current time step, the neural network 110 is configured to receive a feature representation that includes a feature representation generated from features occurring during the current time window time step corresponding to the current time step 230 as well as historical data 232.

As will be described below, the historical data 232 is an optional input and, when used, includes one or more aggregate historical feature representations. Each aggregate historical feature representation represents historical data for the patient aggregated over a corresponding period of time that is longer than the time window corresponding to the current time step.

The neural network 110 includes a deep embedding neural network 240, a deep recurrent neural network 250, a set of main output layers 260, and optionally a set of auxiliary output layers 270.

The deep recurrent neural network 250 and the set of main output layers 260 are collectively referred to as a deep neural network. The deep recurrent neural network 250, the set of main output layers 260, and the set of auxiliary output layers 270 are collectively referred to as a multi-task deep neural network.

The deep embedding neural network 240 includes multiple fully-connected layers and is configured to embed the features in the feature representation in an embedding space. In other words, the deep embedding neural network 240 maps the feature representation into an ordered collection of numeric values, e.g., a vector, in an embedding space that has a fixed dimensionality. By doing so, the embedding neural network 240 transforms the high-dimensional and sparse input feature representation into a lower-dimensional continuous representation that makes subsequent prediction easier. In some implementations, there are residual connections between the fully-connected layers.

In some implementations, the fully-connected layers are L1 regularized. That is, during training, the system uses L1 regularization for the embedding parameters to prevent overfitting and to ensure that the neural network focuses on the most-salient features. Other regularization schemes are also possible.

The deep recurrent neural network 250 includes multiple recurrent neural network ("RNN") layers. In some cases, there are highway connections between the recurrent neural networks in the network e.g., gated connections between RNN layers, optionally skipping one or more layers (arXiv: 1505.00387). The recurrent neural network layers can be any appropriate type of recurrent layers, e.g., simple/standard recurrent units with tan h or other element-wise non-linearity as an activation function, gated recurrent units, long-short term memory, and so on.

The set of main output layers 260 receive the output of the deep recurrent neural network 250 and generate the main output for the main task ("main predictions"), i.e., the neural network output, that is used both during training and to make predictions after training.

As described above, the main output (also referred to as the neural network output) can include a first score that characterizes a predicted likelihood that the adverse health event will occur to the patient within a first time period after the time window corresponding to the last time window time step (the "last time window"). In some cases, the main output can include scores for multiple time periods that each begin after the last time window but that have different durations. Thus, in these cases, the main output includes at least (i) a first score that characterizes a predicted likelihood that the adverse health event will occur to the patient within a first time period after the time window corresponding to the last time window time step and (ii) a second score that characterizes a predicted likelihood that the adverse health event will occur to the patient within a second, longer time period after the time window corresponding to the last time window time step.

In these cases, the main output layers include a linear layer followed by a cumulative distribution function layer. The linear layer generates initial scores for each of the future time periods and the cumulative distribution function layer is configured to generate a cumulative score distribution, e.g., a cumulative probability distribution, over the future time periods that requires the score for each time period to be at least as large as the scores for any other time periods that are shorter than the time period. Because an adverse health event occurring during a shorter time period means that the adverse health event must have occurred during any longer time period that encompasses the shorter time period, this cumulative distribution function layer ensures that the neural network always generates scores that consistently reflect the relative likelihoods of occurrence.

In some implementations the main output layer(s) may output the probability of the adverse health event at each of a set of two or more severity levels; in this case the probabilities may be normalized.

The set of auxiliary output layers 270 receive the output of the deep recurrent neural network 250 and generate an auxiliary output for one or more auxiliary tasks ("auxiliary predictions"). For example, the auxiliary output layers can consist of a single linear layer that makes predictions for all of the auxiliary tasks. An auxiliary task may comprise the task of predicting a value in or derivable from the electronic health record data. The auxiliary tasks are tasks that are used during the training of the neural network to improve the performance of the neural network on the main task but that are not used to make predictions after training. Thus, after training, the neural network includes only the main output layers 260 and does not include the auxiliary output layers 270. In some cases, there are no auxiliary tasks and the network includes only the main output layers 260 both during training and after training.

As an example, the auxiliary outputs can include a respective predicted maximum future observed value for each of one or more medical tests that are correlated with the adverse health event or, more generally, any statistics of future observed values, e.g., mean, median, maximum, minimum, or mode. For example, when the adverse health event is AKI, the auxiliary outputs predict the maximum future observed value of a set of laboratory tests over the same set of time intervals as the future AKI predictions. The laboratory tests predicted are ones that are known to be relevant to kidney function: specifically, the tests can include one or more of creatinine, urea nitrogen, sodium, potassium, chloride, calcium or phosphate. This multi-task approach can in some instances result in better generalization and more-robust representations, especially under class imbalance. In particular, by training the neural network to accurately predict the results of relevant medical tests, the system causes the neural network to generate intermediate representations that more robustly represent the features that are relevant to whether the adverse health event will occur in the future. During training, the system also receives the targets that should have been generated by the neural network (the "main targets" and the "auxiliary targets") and computes a loss based on an error between the main predictions and the main targets and another loss based on an error between the auxiliary targets and the auxiliary predictions. In other words, the system receives the ground truth outputs that reflect the actual future health of the patient. The system then combines the two losses, e.g., by computing a sum or a weighted sum of the two losses, and uses the overall loss to update the values of the parameters of the components of the neural networks, i.e., the main output layers, the auxiliary output layers, the deep recurrent neural network and the deep embedding neural network. That is, embedded features are learnt by the deep embedding neural network by end-to-end training of the system; no pre-training is needed.

For example, the overall loss function can be the weighted sum of the cross-entropy loss from the main task predictions (relative to the main targets) and the squared loss for each of the auxiliary predictions (relative to the corresponding auxiliary target), and the parameters can be updated based on the gradients of the overall loss using an appropriate optimizer, e.g., the Adam optimizer, the rmsProp optimizer, or the stochastic gradient descent optimizer; Xavier initialization may be used. The trained system may be calibrated by plotting a curve of the system's predicted risk against the empirical frequency of the adverse health event for that risk.

In one purely illustrative example implementation the deep embedding neural network has a two-layer perceptron with residual connections and rectified-linear activations, and an embedding layer comprising 400 units for the numerical features and 400 units for the presence features; and the RNN has 3 layers each of 200 units and tan h activations.

Figure 3:
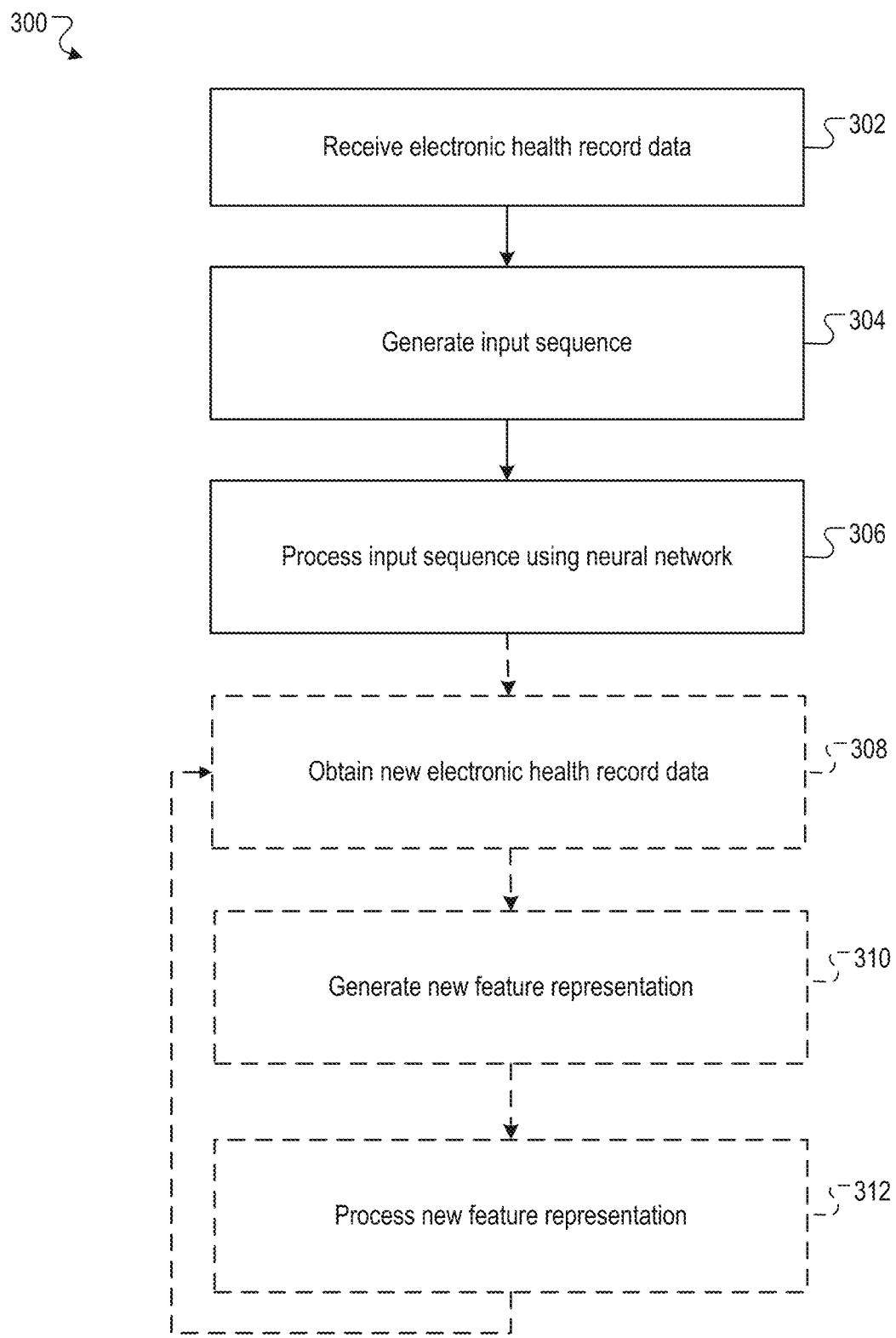
FIG. 3 is a flow diagram of an example process for generating an adverse health event prediction.

FIG. 3 is a flow diagram of an example process 300 for generating an adverse health event prediction. For convenience, the process 300 will be described as being performed by a system of one or more computers located in one or more locations. For example, an adverse health event prediction system, e.g., the adverse health event prediction system 100 of FIG. 1, appropriately programmed, can perform the process 300.

The system receives electronic health record data for a patient (step 302).

The system generates an input sequence from the electronic health record data (304). As described above, the system pre-processes the electronic health record data when generating the input sequence in order to generate an input sequence that can be used by the neural network to make accurate and effective predictions.

In particular, the input sequence generated by the system includes a respective feature representation at each of multiple time steps.

The time steps include multiple time window time steps, i.e., a respective time window time step for each of multiple time windows that each have the same, fixed length. The fixed length can be, e.g., six hours as in the example of FIG. 1 or a different length, e.g., four hours, 12 hours, or one day.

To generate the feature representation for a given time window time step, the system determines, for each of the possible numerical features in the vocabulary and from the electronic health record data, whether the numerical feature occurred during the time window corresponding to the window time step.

The system then generates, for each of the possible numerical features, one or more presence features that identify whether the numerical feature occurred during the time window corresponding to the time window time step and includes the one or more possible presence features in the feature representation for the time step.

Generally, the one or more presence features are each discrete features that can only take one of a small number of possible values. As a particular example, each presence feature can be a binary feature that can only take one of two possible values.

As a particular example, the system can maintain data for each numeric feature that partitions the overall range of the feature into a plurality of ranges. In this example, when the feature did occur during the corresponding time window, the presence features can encode which range from the plurality of ranges the numeric feature belongs to. For example, the presence features can include a respective binary feature for each of the plurality of ranges and the value for the binary feature for the range can be set to a value that indicates that the value falls in the corresponding range, e.g., 1, and the other presence features can be set to a value that indicates that the value did not fall in the corresponding range, e.g., 0. As another example, the presence feature can be a categorical feature that can be set to a different value for each of the ranges, plus a null value that indicates that the numerical feature did not occur.

When the numerical feature did not occur in the time window, the presence features encode that the feature did not occur. For example, when the presence features are binary features as described above, all of the presence features for the feature can bet set to the value that indicates that the value did not fall in the corresponding range.

In some cases, the system includes only the presence features for the numerical feature in the feature representation for the time window time step. For example, the electronic health record data may include only which range the numerical feature falls in. In other cases, the system includes the presence features and the numeric value for the numeric feature that occurred during the time window in the feature representation. Optionally, the system can normalize the numerical value before including the numerical value in the feature representation.

For the discrete features in the vocabulary, the system also encodes the feature using binary presence features as described above and includes the encoded binary presence features in the representation.

When the system determines that, for a particular one of the time windows, the electronic health data does not identify any features as occurring during the time window, the system generates a feature representation for the particular time window time step corresponding to the particular time window time step that indicates that no features occurred during the particular time window. For example, the feature representation for the particular time window time step can be a predetermined feature vector that is only generated for time windows that have no features.

As described above, in some cases, the system occasionally or frequently encounters electronic health record data that does not identify the specific time at which some events occurred, e.g., only identifies the day that they occurred instead of the time of occurrence. This prevents the system from being able to precisely identify which time window the features of these health events correspond to. To account for this, in some implementations the time steps also include multiple surrogate time steps that are inserted at regular intervals among the time window time steps in the sequence. Each surrogate time step is associated with a plurality of time window time steps that immediately precede the surrogate time step in the input sequence, i.e., with all of the time window time steps that are between the surrogate time step and the preceding surrogate time step in the input sequence. For example, when the time windows are six hours long, the system can include a surrogate time step at the conclusion of each day, i.e., after every four time window time steps.

To generate the feature representation for a given surrogate time step, the system determines whether the electronic health record data identifies any features (i) as occurring during a time interval spanned by the time windows corresponding to the plurality of time window time steps associated with the surrogate time steps without (ii) identifying a specific time window during which the feature occurred.

When the electronic health record data does identify at least one such feature, the system generates the feature representation for the surrogate time step from all of these features. In other words, the system gathers the features that do not have specific time windows and generates the feature representation for the surrogate time step as described above, i.e., as if it were a time window time step.

The system can also include other summary data, metadata, or both in each of the feature representations.

For example, the system can map each feature to a corresponding high-level concept, e.g., procedure, diagnosis, prescription, laboratory test, vital sign, admission, transfer and so on. The system can then include in the feature representation at each time step a histogram of frequencies of each high-level concept among the features that occurred at the time step.

As another example, the system can generate and include in the feature representation for each time step at least one aggregate historical feature representation. Each aggregate historical feature corresponds to a respective past time interval. For example, when the time windows are six hours, the system can generate aggregate representation for one or more of: the 48 hours preceding the time window, the 6 months preceding the time window, or the past 5 years preceding the time window.

Each aggregate historical feature representation is based on features occurring within the respective past time interval and includes a summary of the patient's health over the time period. For example, for discrete features, the aggregate representation can include a binary feature that indicates whether the discrete feature was observed during the past time interval or not. For numerical features, the aggregate representation can include various statistics of the occurrences of the numerical feature during the past time interval, e.g., one or more of the count, mean, median, standard deviation, or minimum and maximum value observed in the interval. The aggregate representation may also include trend features for each numerical feature, e.g., the difference between the last observed value of the feature and the minimum or maximum and the average difference between subsequent occurrences of the feature.

In some cases, the system includes time-related metadata in each feature representation. For example, the system can generate and include an age feature based on an age of the patient as of the time window corresponding to the time window time step. As another example, the system can generate and include a time feature identifying the time window corresponding to the time window time step. For example, the time feature can identify one or more of the date during which the time window occurred or the time of day during which the time window occurred.

The system processes the input sequence using the neural network to generate a neural network output that characterizes a predicted likelihood that an adverse health event will occur to the patient after the time window corresponding to the last time window time step in the input sequence (step 306).

The system can then update the neural network output as more information is received. For example, the system can performs steps 302-306 when the patient is first admitted for treatment. The system can then generate an updated neural network output as each subsequent time window elapses.

In particular, the system can repeatedly perform steps 308-312 to repeatedly generate updated neural network outputs.

The system receives new electronic health record data (step 308). The new electronic health record data is data for the most recent time window that has elapsed.

The system generates a new feature representation for the most recent time window using the new electronic health record data (step 310). As described above, in some implementations, the new feature representation also includes one or more aggregate historical feature representations.

The system processes the new feature representation using the neural network to generate a new neural network output (step 312). Because, as described above, the neural network includes recurrent neural network layers, the system considers the previous feature representations that have been processed, i.e., through the maintained internal states of the recurrent layers.

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

This approach to training an object interaction task neural network can reduce the number of task episodes required to train the neural network and can result in an improved trained neural network without requiring additional supervision for the training process.

Training of the object interaction task neural network may therefore require fewer computational resources. An improved trained object interaction task neural network can facilitate improved robotic control.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs. The one or more computer programs can comprise one or more modules of computer program instructions encoded on a tangible non transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a data communication network.

In this specification, the term "database" is used broadly to refer to any collection of data: the data does not need to be structured in any particular way, or structured at all, and it can be stored on storage devices in one or more locations. Thus, for example, the index database can include multiple collections of data, each of which may be organized and accessed differently.

Similarly, in this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer readable media suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Data processing apparatus for implementing machine learning models can also include, for example, special-purpose hardware accelerator units for processing common and compute-intensive parts of machine learning training or production, i.e., inference, workloads.

Machine learning models can be implemented and deployed using a machine learning framework, e.g., a TensorFlow framework, a Microsoft Cognitive Toolkit framework, an Apache Singa framework, or an Apache MXNet framework.

Embodiments of the subject matter described in this specification can be implemented in a computing system that includes a back end component, e.g., as a data server, or that includes a middleware component, e.g., an application server, or that includes a front end component, e.g., a client computer having a graphical user interface, a web browser, or an app through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A system comprising one or more computers and one or more storage devices storing instructions that, when executed by the one or more computers, cause the one or more computers to perform operations comprising:
   receiving electronic health record data for a patient, the electronic health data comprising a plurality of features representing health events in an electronic health record for the patient, each of the plurality of features belonging to a vocabulary of possible features that comprises a plurality of possible numerical features and a plurality of possible discrete features;
   generating, from the electronic health record data, an input sequence comprising a respective feature representation at each of a plurality of time steps, wherein the plurality of time steps comprises a respective time window time step for each of a plurality of time windows and one or more surrogate time steps, each surrogate time step associated with a plurality of preceding time window time steps that immediately precede the surrogate time step in the input sequence, the generating comprising:

for each of a plurality of time window time steps:
determining, for each of the possible numerical features and from the electronic health record data, whether the numerical feature occurred during the time window corresponding to the time window time step;
generating, for each of the possible numerical features, one or more presence features that, identify whether the numerical feature occurred during the time window corresponding to the time window time step; and
including the one or more possible presence features in the feature representation for the time window time step, comprising, for each of the possible numerical features, when the numerical feature occurred during the time window corresponding to the time window time step including both (i) a numerical value for the numeric feature that is identified as occurring during the time window corresponding to the time window time step in the electronic health record data and (ii) one or more presence features that identify that the numerical feature occurred during the time window corresponding to the time window time step; and for each of the one or more surrogate time steps:
determining whether the electronic health record data identifies, for any feature, only that the feature (i) occurred during a time interval spanned by the time windows corresponding to the plurality of preceding time window time steps associated with the surrogate time step without (ii) identifying any time window during which the feature occurred; and
when the electronic health record data does identify at least one feature (i) as occurring during a time interval spanned by the time windows corresponding to the plurality of preceding time window time steps associated with the surrogate time step without (ii) identifying any time window during which the feature occurred:
generating the feature representation for the surrogate time step from at least the at least one feature;
determining that the electronic health data does not identify any features as occurring during a time window corresponding to a particular time window time step; and
generating a feature representation for the particular time window time step that indicates that no features occurred during the corresponding time window, wherein the feature representation for the particular time window time step is a predetermined feature vector that is only generated for time windows that have no features; and processing the input sequence using a neural network to generate a neural network output that characterizes a predicted likelihood that an adverse health event will occur to the patient after the time window corresponding to the last time window time step in the input sequence.

2. The system of claim 1, wherein the plurality of possible features comprise a plurality of clinical features, wherein each clinical feature is mapped to a corresponding concept, and wherein generating the feature representation comprises, at each of the plurality of time window time steps:
generating a histogram of frequencies of each concept among the features that occurred at the time window time step; and
including the histogram in the feature representation for the time window time step.

3. The system of claim 1, wherein generating the feature representation comprises, at each of the plurality of time window time steps:
generating at least one aggregate historical feature representation, each aggregate historical feature representation corresponding to a respective past time interval, and each aggregate historical feature representation being based on features occurring within the respective past time interval of the time window corresponding to the time window time step; and
including the at least one aggregate historical feature representation in the feature representation for the time window time step.

4. The system of claim 1, wherein generating the feature representation comprises, at each of the plurality of time window time steps:
generating an age feature based on an age of the patient as of the time window corresponding to the time window time step; and
including the age feature in the feature representation for the time window time step.

5. The system of claim 1, wherein generating the feature representation comprises, at each of the plurality of time window time steps:
generating a time feature identifying the time window corresponding to the time window time step; and
including the time feature in the feature representation for the time window time step.

6. The system of claim 1, wherein the neural network comprises:
a deep embedding neural network comprising a plurality of fully-connected layers and configured to, for each feature representation:
embed the features in the feature representation in an embedding space; and
a deep neural network configured to:
generate the neural network output from the embedded features.

7. The system of claim 6, wherein the deep embedding neural network has residual connections between the fully-connected layers.

8. The system of claim 6, wherein the deep embedding neural network is L1 regularized.

9. The system of claim 1, wherein the neural network comprises a plurality of recurrent neural network layers.

10. The system of claim 9, wherein the recurrent neural network layers have highway connections.

11. The system of claim 1, wherein the neural network output includes at least a first score that characterizes a predicted likelihood that the adverse health event will occur to the patient within a first time period after the time window corresponding to the last time window time step.

12. The system of claim 1, wherein the neural network output includes at least (i) a first score that characterizes a predicted likelihood that the adverse health event will occur to the patient within a first time period after the time window corresponding to the last time window time step and (ii) a second score that characterizes a predicted likelihood that the adverse health event will occur to the patient within a second, longer time period after the time window corresponding to the last time window time step.

13. The system of claim 12, wherein the neural network includes a cumulative distribution function layer configured to generate a cumulative score distribution over at least the first time window and the second time window that requires the second score to be higher than the first score.

14. The system of claim 1, wherein the neural network output includes a respective predicted maximum future observed value for each of one or more medical tests that are correlated with the adverse health event.

15. The system of claim 1, the operations further comprising;
    determining whether the neural network output indicates that the predicted likelihood exceeds a threshold; and
    when the neural network output indicates that the predicted likelihood exceeds a threshold, transmitting an alert for presentation to a user.

16. The system of claim 1, the operations further comprising:
    generating, from the neural network output, user interface data for presentation to a user; and
    outputting the user interface data.

17. The system of claim 1, the operations further comprising:
    obtaining new electronic health record data comprising features occurring at a next time window immediately after the last time window corresponding to the last time window time step in the input sequence;
    generating a new feature representation from the new electronic health record data; and
    processing the new feature representation using the neural network generate a new neural network output.

18. The system of claim 1, wherein the neural network output includes a respective predicted statistic for future observed values for each of one or more medical tests that are correlated with the adverse health event.

19. The system of claim 1, wherein each presence feature is a binary feature.

20. One or more non-transitory computer-readable storage media storing instructions that when executed by one or more computers cause the one or more computers to perform operations comprising:
    receiving electronic health record data for a patient, the electronic health data comprising a plurality of features representing health events in an electronic health record for the patient, each of the plurality of features belonging to a vocabulary of possible features that comprises a plurality of possible numerical features and a plurality of possible discrete features;
    generating, from the electronic health record data, an input sequence comprising a respective feature representation at each of a plurality of time steps, wherein the plurality of time steps comprises a respective time window time step for each of a plurality of time windows and one or more surrogate time steps, each surrogate time step associated with a plurality of preceding time window time steps that immediately precede the surrogate time step in the input sequence, the generating comprising:
        for each of a plurality of time window time steps:
            determining, for each of the possible numerical features and from the electronic health record data, whether the numerical feature occurred during the time window corresponding to the time window time step;
            generating, for each of the possible numerical features, one or more presence features that identify whether the numerical feature occurred during the time window corresponding to the time window time step; and
            including the one or more possible presence features in the feature representation for the time window time step, comprising, for each of the possible numerical features, when the numerical feature occurred during the time window corresponding to the time window time step including both (i) a numerical value for the numeric feature that is identified as occurring during the time window corresponding to the time window time step in the electronic health record data and (ii) one or more presence features that identify that the numerical feature occurred during the time window corresponding to the time window time step; and
        for each of the one or more surrogate time steps:
            determining whether the electronic health record data identifies, for any feature, only that the feature (i) occurred during a time interval spanned by the time windows corresponding to the plurality of preceding time window time steps associated with the surrogate time step without (ii) identifying any time window during which the feature occurred; and
            when the electronic health record data does identify at least one feature (i) as occurring during a time interval spanned by the time windows corresponding to the plurality of preceding time window time steps associated with the surrogate time step without (ii) identifying any time window during which the feature occurred:
                generating the feature representation for the surrogate time step from at least the at least one feature;
            determining that the electronic health data does not identify any features as occurring during a time window corresponding to a particular time window time step; and
            generating a feature representation for the particular time window time step that indicates that no features occurred during the corresponding time window, wherein the feature representation for the particular time window time step is a predetermined feature vector that is only generated for time windows that have no features; and
    processing the input sequence using a neural network to generate a neural network output that characterizes a predicted likelihood that an adverse health event will occur to the patient after the time window corresponding to the last time window time step in the input sequence.

21. A computer-implemented method comprising:
    receiving electronic health record data for a patient, the electronic health data comprising a plurality of features representing health events in an electronic health record for the patient, each of the plurality of features belonging to a vocabulary of possible features that comprises a plurality of possible numerical features and a plurality of possible discrete features;
    generating, from the electronic health record data, an input sequence comprising a respective feature representation at each of a plurality of time steps, wherein the plurality of time steps comprises a respective time window time step for each of a plurality of time windows and one or more surrogate time steps, each surrogate time step associated with a plurality of preceding time window time steps that immediately precede the surrogate time step in the input sequence, the generating comprising:

for each of a plurality of time window time steps:
  determining, for each of the possible numerical features and from the electronic health record data, whether the numerical feature occurred during the time window corresponding to the time window time step;
  generating, for each of the possible numerical features, one or more presence features that, identify whether the numerical feature occurred during the time window corresponding to the time window time step; and
  including the one or more possible presence features in the feature representation for the time window time step, comprising, for each of the possible numerical features, when the numerical feature occurred during the time window corresponding to the time window time step including both (i) a numerical value for the numeric feature that is identified as occurring during the time window corresponding to the time window time step in the electronic health record data and (ii) one or more presence features that identify that the numerical feature occurred during the time window corresponding to the time window time step; and
for each of the one or more surrogate time steps:
  determining whether the electronic health record data identifies, for any feature, only that the feature (i) occurred during a time interval spanned by the time windows corresponding to the plurality of preceding time window time steps associated with the surrogate time step without (ii) identifying any time window during which the feature occurred; and
  when the electronic health record data does identify at least one feature (i) as occurring during a time interval spanned by the time windows corresponding to the plurality of preceding time window time steps associated with the surrogate time step without (ii) identifying any time window during which the feature occurred:
    generating the feature representation for the surrogate time step from at least the at least one feature;
  determining that the electronic health data does not identify any features as occurring during a time window corresponding to a particular time window time step; and
  generating a feature representation for the particular time window time step that indicates that no features occurred during the corresponding time window, wherein the feature representation for the particular time window time step is a predetermined feature vector that is only generated for time windows that have no features; and
  processing the input sequence using a neural network to generate a neural network output that characterizes a predicted likelihood that an adverse health event will occur to the patient after the time window corresponding to the last time window time step in the input sequence.

22. The method of claim 21, wherein the plurality of possible features comprise a plurality of clinical features, wherein each clinical feature is mapped to a corresponding concept, and wherein generating the feature representation comprises, at each of the plurality of time window time steps:
  generating a histogram of frequencies of each concept among the features that occurred at the time window time step; and
  including the histogram in the feature representation for the time window time step.

23. The method of claim 21, wherein generating the feature representation comprises, at each of the plurality of time window time steps:
  generating at least one aggregate historical feature representation, each aggregate historical feature representation corresponding to a respective past time interval, and each aggregate historical feature representation being based on features occurring within the respective past time interval of the time window corresponding to the time window time step; and
  including the at least one aggregate historical feature representation in the feature representation for the time window time step.

24. The method of claim 21, wherein generating the feature representation comprises, at each of the plurality of time window time steps:
  generating an age feature based on an age of the patient as of the time window corresponding to the time window time step; and
  including the age feature in the feature representation for the time window time step.

25. The method of claim 21, further comprising discarding the neural network output generated by the neural network based on processing the feature representation for the surrogate time step.

* * * * *